United States Patent [19]

Klaus et al.

[11] Patent Number: 4,935,560
[45] Date of Patent: Jun. 19, 1990

[54] NOVEL TETRAHYDRONAPHTHALENE & INDANE DERIVATIVES

[75] Inventors: Michael Klaus, Weil am Rhein, Fed. Rep. of Germany; Peter Loeliger, Muttenz; Peter Mohr, Basel, both of Switzerland; Ekkehard Weiss, Inzlingen, Fed. Rep. of Germany

[73] Assignee: Hoffmann-La Roche Inc., Nutley, N.J.

[21] Appl. No.: 467,291

[22] Filed: Jan. 16, 1990

Related U.S. Application Data

[60] Continuation of Ser. No. 406,885, Sep. 11, 1989, abandoned, which is a continuation of Ser. No. 350,279, May 11, 1989, abandoned, which is a division of Ser. No. 49,916, May 16, 1987, Pat. No. 4,870,219.

[30] Foreign Application Priority Data

May 23, 1986 [CH] Switzerland ............ 2091/86
Mar. 17, 1987 [CH] Switzerland ............ 984/87

[51] Int. Cl.$^5$ ............ C07C 21/18; C07C 33/50; C07C 43/18; C07C 43/192
[52] U.S. Cl. .................. 570/189; 568/608; 568/626; 568/630; 568/632; 568/634; 568/636; 568/654; 568/669; 568/807; 568/808; 568/811; 568/812; 568/828; 568/832; 568/838
[58] Field of Search ............ 570/189; 568/608, 626, 568/630, 634, 654, 632, 669, 807, 808, 811, 812, 828, 832, 838

[56] References Cited

U.S. PATENT DOCUMENTS

| 3,822,305 | 7/1974 | Pintschovius | 570/189 |
|---|---|---|---|
| 4,193,931 | 3/1980 | Loeliger et al. | 570/189 |
| 4,376,055 | 4/1982 | Loeliger | 570/189 |
| 4,396,553 | 8/1983 | Klaus | 260/456 |
| 4,588,750 | 4/1980 | Boris | 570/189 |
| 4,714,786 | 12/1987 | Wuest et al. | 570/189 |

FOREIGN PATENT DOCUMENTS

| 47834/85 | 3/1986 | Australia . | |
| 47836/85 | 4/1986 | Australia . | |
| 1087212 | 10/1980 | Canada . | |
| 0176034 | 4/1986 | European Pat. Off. . | |
| 3715955 | 11/1987 | Fed. Rep. of Germany | 570/189 |
| 1561244 | 4/1977 | United Kingdom . | |
| 2164938 | 9/1984 | United Kingdom . | |

OTHER PUBLICATIONS

Klaus et al., "Chemical Abstracts", vol. 100(17), 139382 c (1983).
Klaus et al., "Chemical Abstracts", vol. 108(11), 9427c (1988).
Carruthers, J. Chem. Soc. (C), 1967, 1525.
Subramaniam, J. Liquid Chromatography 7 (7), 1455 (1984).
Cunningham, J. Chem. Soc., 1963, 2875–2883.
Ciba Foundation Symposium, Retinoids 1–27 (1985).
Loeliger, Eur. J. Med. Chem-Chimica Therapeutica, Jan., Feb., 1980, 15 No. 1.

*Primary Examiner*—Werren B. Lone
*Attorney, Agent, or Firm*—George M. Gould; Bernard S. Leon; William H. Epstein

[57] ABSTRACT

Novel styryl-tetrahydromaphthalene and indane derivatives useful for treating neoplasms and dermatoses.

4 Claims, No Drawings

NOVEL TETRAHYDRONAPHTHALENE & INDANE DERIVATIVES

This application is a continuation of application Ser. No. 07/406,885, filed 9/11/89, which in turn is a continuation of Ser. No. 07/350,279 filed 5/11/89 both abandoned which in turn is a divisional of Ser. No. 07/049,916 filed 5/16/87 now U.S. Pat. No. 4,870,219.

SUMMARY OF INVENTION

The present invention is concerned with novel tetrahydronaphthalene and indane derivatives of the formula

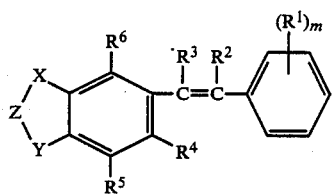

wherein X and Y is

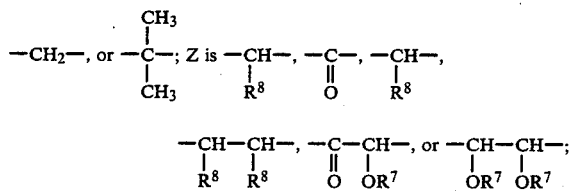

$R^1$ is fluorine, chlorine iodine, o-bromo, m-bromo, lower-alkoxy acyloxy, nitro, hydroxy amino, lower-alkylamino, di-lower-alkylamino or phenyl; or lower alkyl in the o- or m-position: $R^2$ and $R^3$ are hydrogen. lower-alkyl. trifluoromethyl or halogen with one of $R^2$ and $R^3$ being hydrogen, trifluoromethyl or lower-alkyl. $R^4$ and $R^5$ are hydrogen alkyl, alkoxy or halogen; $R^6$ halogen, lower-alkoxy alkyl or —$OR^7$; $R^7$ is nydrogen lower-alkyl or acyl; $R^8$ is hydrogen or lower-alkyl: m is a whole number of from 0 to 5. with the proviso that when m is O and Z is —$CH_2$—$CH_2$—, $R^6$ is hydrogen; and with the exception of 1,2,3,4-tetrahydro-1,1,4,4-tetramethyl-6-(α-methylstyryl)naphthalene and its derivatives which are hydroxylated in the terminal phenyl ring.

The compound of formula I are useful as for combatting dermatoses as well as neoplasmas

DETAILED DESCRIPTION

The expression "lower" relates to groups with 1–6 C-atoms. Alkyl and alkoxy groups can be straight-chain or branched such as methyl, ethyl, propyl, isopropyl butyl, and sec.-butyl and methoxy, ethoxy, propoxy, isopropoxy, butoxy and sec.-butoxy, respectively. Alkyl and alkoxy groups $R^4$ and $R^5$ preferably contain from 1 to 10 carbon atoms such as octyl, nonyl, decyl and 2,2-dimethyloctyl and octyloxy, nonyloxy, decyloxy and 2,2-dimethyloctyloxy, respectively. Examples of acyloxy groups are alkanoyloxy groups, preferably loweralkanoyloxy groups containing from 2 to 6 carboratoms such as acetoxy, propionyloxy, butyryloxy pivaloyloxy and caproyloxy; or aroyloxy groups such as benzoyloxy, p-nitrobenzoyloxy and toluoyloxy; or aralkanoyloxy groups such as phenylacetoxy. Halogen embraces fluorine, chlorine, bromine and iodine.

The compounds of formula I can exist as trans or cis isomers or as cis/trans isomer mixtures In general, the trans compounds of formula I are preferred.

Of the compounds of formula I there are furthermore preferred those in which X and Y is a group —C(CH$_3$)$_2$— and those in which m=1 or 2 or 3, especially 1. With respect to the substitutents $R^2$ and $R^3$, hydrogen is preferred for $R^2$ and lower-alkyl, especially methyl, is preferred for $R^3$. $R^4$ is preferably hydrogen or alkyl or alkoxy with up to 10 C-atoms. $R^5$ and $R^6$ are preferably hydrogen.

Among the preferred compound of formula I are the following compounds:

Compounds of the formula:

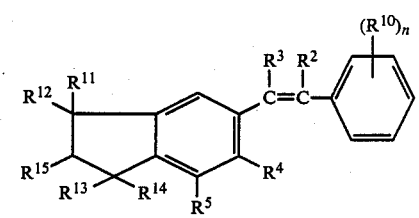

wherein n is an integer of from 1 to 3, $R^2$, $R^3$, $R^4$ and $R^5$ are as above,; $R^{11}$, $R^{12}$, $R^{13}$, and $R^{14}$ are hydrogen or methyl, $R^{10}$, is fluorine chlorine, iodine, o-oromo or meta-bromo; and $R^{15}$ is hydrogen, oxo, lower alkyl acyloxy hydroxy or lower alkoxy: and Compounds of the formula:

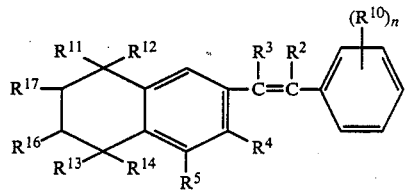

wherein n, $R^2$, $R^3$, $R^4$, $R^5$, $R^{10}$, $R^{11}$, $R^{12}$, $R^{13}$, and $R^{14}$ are as above; $R^{16}$ and $R^{17}$ are hydrogen, oxo, lower alkyl, acyloxy, hydroxy, or lower alkoxy with the proviso that both $R^{16}$ and $R^{17}$ are not oxo;

Compounds of the formula:

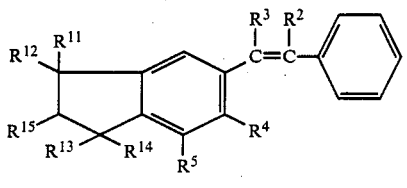

wherein n, $R^2$, $R^3$, $R^4$, $R^5$, $R^{11}$, $R^{12}$, $R^{13}$, R14, $R^{16}$ and $R^{17}$ are as above; and Compounds of the formula:

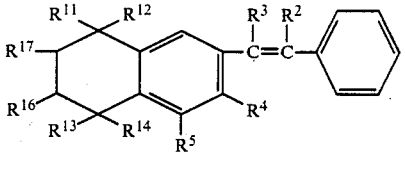

wherein n, $R^2$, $R^3$, $R^4$, $R^5$, $R^{11}$, $R^{12}$, $R^{13}$, $R^{14}$, $R^{16}$ and $R^{17}$ are as above; with the proviso that when $R^3$ is methyl and $R^4$ is hydrogen, at least one of $R^{11}$, $R^{12}$, $R^{13}$ or $R^{14}$ is hydrogen;

Compounds of the formula:

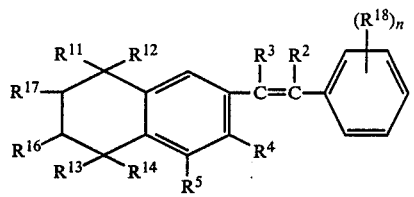   I-E wherein n, $R^2$, $R^3$, $R^4$, $R^5$, $R^{11}$, $R^{12}$, $R^{13}$, $R^{14}$, $R^{16}$ and $R^{17}$ are as above; and $R^{18}$ is lower alkyl with at least one lower alkyl group located in the ortho or meta positions:

Compounds of the formula:

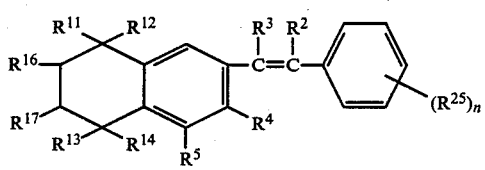   I-F wherein n, $R^2$, $R^3$, $R^4$, $R^5$, $R^{11}$, $R^{12}$, $R^{13}$, $R^{14}$, $R^{16}$ and $R^{17}$ are as above; and $R^{25}$ is nitro, amino or lower alkylamino;

Compounds of the formula:

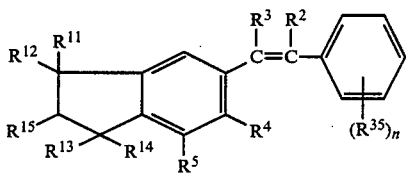   I-G wherein n, $R^2$, $R^3$, $R^4$, $R^5$, $R^{11}$, $R^{12}$, $R^{13}$, $R^{14}$, and $R^{15}$ are as above; and $R^{35}$ is hydroxy, lower alkoxy or acyloxy; and Compounds of the formula:

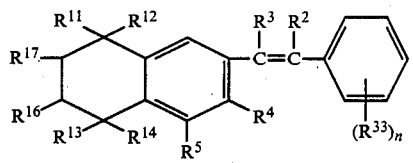   I-H wherein n, $R^2$, $R^3$, $R^4$, $R^5$, $R^{11}$, $R^{12}$, $R^{13}$, $R^{14}$, and $R^{16}$ and $R^{17}$ are as above; and $R^{33}$ is lower alkoxy or acyloxy; and Compounds of the formula:

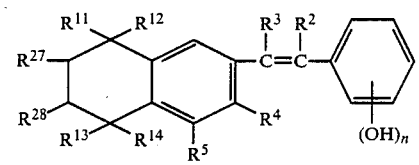   I-J wherein n, $R^2$, $R^3$, $R^4$, $R^5$, $R^{11}$, $R^{12}$, $R^{13}$ and $R^{14}$ are as above; and $R^{27}$ and $R^{28}$ are oxo, acyloxy, hydroxy or lower alkoxy with the proviso that $R^{27}$ and $R^{28}$ are not both oxo.

The invention is also concerned with a process for the manufacture of the compounds of formula I, pharmaceutical preparations based on the compounds of formula I, the compounds of formula I in the treatment and prophylaxis of neoplasms and dermatoses as well as the use of the compounds of formula I in the manufacture of pharmaceutical preparations for the treatment and prophylaxis of such conditions.

The compounds of formula I can be manufactured in accordance with the invention by reacting a compound of the general formula

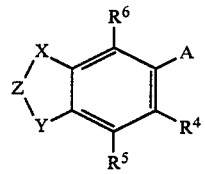   II with a compound of the general formula

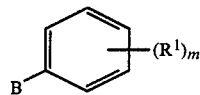   III in which either

A is a residue —$CH(R^3)P^+(Q)_3Y^-$ or —$CH(R^3)P(O)(OAlk)_2$ and B is a residue $R^{21}$—CO—; or A is a residue $R^{31}$—CO— and B is a residue —$CH(R^2)P^+(Q)_3Y^-$ or —$CH(R^2)P(O)(OAlk)_2$ or —$CH(R^{21})MgHal$; or A is a residue —$CH(R^{31})MgHal$ and B is a residue $R^2$—CO—; whereby in the above formulae Q is aryl; $Y^-$ is the anion of an organic or inorganic acid; Alk is a lower alkyl group; Hal is halogen; $R^{21}$ and $R^{31}$ are hydrogen, trifluoromethyl or lower-alkyl; and $R^1$, $R^2$, $R^3$, $R^4$, $R^5$, X, Y, Z and m have the significance given above and the manufacture of 1,2,3,4-tetrahydro-1,1,4,4-tetramethyl-6-(α-methylstyryl)naphthalene and its derivatives which are hydroxylated in the terminal phenyl ring is excluded, whereupon, if desired, a nitro group $R^1$ is reduced to the amino group, if desired an amino group $R^1$ is mono- or di-alkylated, if desired an acyloxy group $R^1$ or $R^7$ is saponified, a carbonyl group obtained in Z is reduced to the hydroxy group and, if desired, a hydroxy group $R^1$ or $R^7$ or a hydroxy group obtained in Z is alkylated or acylated.

The reaction of the compounds of formulae II and III can be carried out according to the known methods of the Wittig, Horner or Grignard reaction.

In the case of the Wittig reaction, i.e. with the use of a compound of formula II with A= —$CH(R^3)P^+(Q)_3Y^-$ or of formula III with B= —$CH(R^2)P^+(Q)_3Y^-$, components are reacted with one another in the presence of an acid-binding agent, e.g. in the presence of a strong base such as e.g. butyllithium, sodium hydride or the sodium salt of dimethyl sulphoxide, but especially in the presence of an optionally lower alkyl-substituted ethylene oxide such as 1,2-butylene oxide, optionally in a solvent. e.g. in an ether such as diethyl ether or tetrahydrofuran or in an aromatic hydrocarbon such as benzene, in a temperature range lying between room temperature and the boiling point of the reaction mixture.

Of the inorganic acid ions $Y^-$ the chloride ion, the bromide ion or the hydrosulphate ion is preferred and of the organic acid ions the tosyloxy ion is preferred. The aryl residue Q is preferably a phenyl residue or a substituted phenyl residue such as P-tolyl.

In the case of the Horner reaction, i.e. with the use of a compound of formula II with $A = -CH(R^3)-P(O)-(OAlk)_2$ or of formula III with $B = -CH(R^2)-P(O)-(OAlk)_2$ the components are condensed with the aid of a base and preferably in the presence of an inert organic solvent. e.g. with the aid of sodium hydride in benzene, toluene, dimethylformamide, tetrahydrofuran, dioxan or 1,2-dimethoxyethane, or also with the aid of a sodium alcoholate in an alkanol, e.g. sodium methylate in methanol, in a temperature range lying between 0° and the boiling point of the reaction mixture.

The alkoxy residues OAlk are especially lower alkoxy residues with 1-6 carbon atoms such as methoxy or ethoxy.

The reaction of a compound of formula II with $A = -CH(R^{31})MgHal$ or of formula III with $B = -CH(R^{21})MgHal$ can be carried out in a manner known per se under the conditions of a Grignard reaction, e.g. in an ether such as diethyl ether or tetrahydrofuran at room temperature and subsequent water-cleavage with acidic agents, e.g. with organic acids such as p-toluenesulphonic acid.

Compounds of formula I which contain an amino group in the phenyl ring (i.e. in which a residue $R^1$ is amino) are conveniently manufactured via the corresponding nitro compounds. A nitro group present in a compound of formula I can be converted into an amino group in a manner known per se by reduction, e.g. with nascent hydrogen. An amino group present in a compound I can be mono- or di-alkylated in a manner known per se. e.g. by treatment with alkilating agents such as alkyl halides or alkyl sulphates or by reductive alkylation with aldehydes such as formaldehyde or acetaldehyde and sodium cyanoborohydride. The reduction of a carbonyl group contained in Z as well as the alkylation and acylation of hydroxy groups can also be carried out in a manner known per se. For example, a carbonyl group can be reduced to the hydroxy group by treatment with reduction agents such as sodium borohydride.

The compounds of formula I can exist in trans or cis form. In the process they are mainly obtained in the trans form. Cis components which may be obtained can be separated, if desired, in a manner known per se.

The starting materials of formulae II and III, insofar as their preparation is not known or is not described hereinafter, can be prepared in analogy to known methods or to methods described hereinafter.

The compounds of formula I are therapeutically active. In particular, they possess antiseborrhoeic, antikeratinizing, anti-neoplastic and anti-allergic/anti-inflammatory activity, which can be demonstrated using the test procedures described hereinafter:

(A) The antikeratinizing activity can be determined on the rhino mouse model according to the following procedure. The skin of the rhino mouse is characterized by the presence of keratin-filled utriculi of the epidermis and subcutaneous cysts, both of which are derived from hair follicles. The administration of retinoids leads to a hyperproliferation of the epidermis and of the epithelial lining of the utriculi. The thickening of the epidermis and the reduction in the size of the utriculi lead to a normalization of the altered structure of the epithelial layer. The daily topical application of 0.1 ml/cm$^2$ skin of the rhino mouse of a 3% acetone solution of an active test compound over a period of 3 weeks or the thrice weekly oral administration in arachis oil over a period of 3 weeks leads to a significant proliferation of the epidermis and a striking reduction of the keratin-filled utriculi.

(B) The activity in the prevention of chemically-induced breast tumours can be determined according to the following procedure. Female Sprague-Dawley rats are kept under temperature-controlled and light-controlled conditions, with free access to drinking water and feed. At the age of 50 days 15 mg of dimethylbenz-(a)anthracene disolved in arachis oil are administered to each rat by means of a probang. The treatment with the test compounds begins 1 day after the administration of the carcinogen. The body weights of the test animals are recorded and the tumours are palpated weekly and measured with a vernier caliper. The volumes are calculated according to the formula $$\frac{D}{2} \cdot d^2$$

in which D is the larger diameter of the tumour ellipsoid and d is the smaller diameter of the tumour ellipsoid. After 11 weeks the test is terminated and evaluated. In this test there are used in addition to 30 control animals, which receive exclusively normal feed, the following two groups of test animals:

1. 33 rats to which are administered daily 30 mg/kg of test compound mixed with the feed.
2. 36 rats to which are administered daily 90 mg/kg of test compound mixed with the feed.

(C) Furthermore, the activity on tumours can be determined on the transplantable chondrosarcoma of the rat according to the following method. The solid tumour of a donor animal is finely minced and suspended in phosphate buffer/sodium chloride solution. 0.5 ml of the 30% tumour suspension is implanted subcutaneously into albino rats.

The transplanted rats are divided into test groups of in each case 8 animals. The test compounds are suspended in arachis oil and administered orally five times per week for 24 days. The tumours are excised and weighed on day 24. The results are expressed in the quotient C/T which is calculated as follows:

$$C/T = \frac{\text{Average tumour weight of control}}{\text{Average tumour weight of treated}}.$$

(D) The antimetaplastic activity can also be determined in rats according to the following method. Female Holtzmann rats weighing approximately 100 g are ovarectomized under Thiogenal narcosis after an adaptation period of 8 days and are used in the test after a further 14 days. In each case two animals are placed in a cage with free access to feed which contains approximately 2000 IU of vitamin A determined analytically. Prior to the oral administration of the test compound the animals are treated subcutaneously each day on 6 successive days with 1 µg of estradiol benzoate and 250 µg of testosterone propionate dissolved in 0.1 ml of sesame oil. The parenteral hormone administration leads to the formation of a clear granular stage in the vaginal smear, i.e. a squamous metaplasia. 2 days after the oral administration of the test substance the result of the reaction is again read off on the vaginal epithelium. The area method according to Behrens and Karber is employed to calculate the average effective dosages.

(E) The activity of the compounds I on sebum secretion in rats was determined according to the following procedure. Male rats of approximately 50-60 g body weight were castrated at the age of 21-22 days. One week after this operation the rats were washed in a cleansing solution in order to remove sebum which was excreted prior to the test period. Only the carrier materials used were administered to one group of rats. A further group of rats also simultaneously received 100 μg of testosterone propionate in 0.2 ml of sesame oil per rat and day. To a further group of rats there were administered daily per rat 100 μg of testosterone propionate in 0.2 ml of sesame oil subcutaneously and the test compounds in various dosages in 0.2 ml of propylene glycol orally. The rats were thus treated for 14 days. On the 15th day the sebum from the skin surface and the pelt was removed by immersing the entire body of the test animals in a determined volume of acetone and bathing therein for 2 minutes. An aliquot of the solvent bath was evaporated and the solid residue was determined gravimetrically. The inhibition of the testosterone-stimulated increase in the serum secretion in comparison to the corresponding values from rats treated only with testosterone propionate was used as the measurement for the activity.

The results of these tests A-E with compounds of formula I are presented in Tables I-V hereinafter.

TABLE I (A) Anti-keratinizing activity in the rhino mouse

| Compound | Dosage [mg/kg] p.o. | Diameter of the utriculus [μm] | Reduction [%] |
|---|---|---|---|
| a | 0 | 151 | |
|   | 400 | 117 | 21 |
| b | 0 | 161 | |
|   | 400 | 131 | 19 |
| c | 0 | 125 | |
|   | 133 | 91 | 27 |
|   | 400 | 61 | 51 |
| d | 0 | 168 | |
|   | 133 | 125 | 27 |

TABLE II (B) Prophylaxis of chemically-induced breast tumours

| Compound | Dosage [mg/kg] p.o. | Rats with tumours [% of controls] | Average number of tumours per rat [% of controls] | Average tumour volume per rat in mm³ [% of controls] |
|---|---|---|---|---|
| a | 30 | 72 | 47 | 22 |
|   | 90 | 69 | 42 | 22 |
| b | 30 | 106 | 87 | 90 |
|   | 90 | 99 | 87 | 43 |
| c | 30 | 92 | 56 | 78 |
|   | 90 | 85 | 43 | 32 |

TABLE III (C) Activity on transplatable chondrosarcoma of the rat

| Compound | Dosage [mg/kg] p.o. | Quotient C/T of tumour weight of the untreated control animals and of the treated animals |
|---|---|---|
| b | 120 | 1.6 |
| c | 40 | 2.0 |
|   | 120 | 24.0 |

TABLE III-continued (C) Activity on transplatable chondrosarcoma of the rat

| Compound | Dosage [mg/kg] p.o. | Quotient C/T of tumour weight of the untreated control animals and of the treated animals |
|---|---|---|
| f | 120 | 1.6 |

TABLE IV (D) Antimetaplastic activity in the rat

| Compound | Relative activity |
|---|---|
| all-Trans-retinoic acid | 1 |
| a | 0.87 |
| b | 0.77 |
| c | 1.04 |

TABLE V (E) Inhibition of sebum production in the rat

| Compound | Dosage [μg/rat] p.o. | Inhibition of testosterone-stimulated sebum secretion [%] |
|---|---|---|
| a | 100 | 67 |
| b | 100 | 65 |
| e | 100 | 71 |
| g | 100 | 71 | a: (E)-6-(p-Fluoro-α-methylstyryl)-1,2,3,4-tetrahydro-1,1,4,4-tetramethylnaphthalene
b: (E)-6-(p-Bromo-α-methylstyryl)-1,2,3,4-tetrahydro-1,1,4,4-tetramethylnaphthalene
c: 1,2,3,4-Tetrahydro-6-[(E)-p-methoxy-α-methylstyryl]-1,1,4,4-tetramethylnaphthalene
d: 1,1,3,3-Tetramethyl-5-[(E)-α-methylstyryl]indane
e: (E)-6-(p-Iodo-α-methylstyryl)-1,2,3,4-tetrahydro-1,1,4,4-tetramethylnaphthalene
f: (E)-6-(p-Chloro-α-methylstyryl)-1,2,3,4-tetrahydro-1,1,4,4-tetramethylnaphthalene
g: 1,2,3,4-Tetrahydro-1,1,4,4-tetramethyl-6-(α-methyl-styryl)-7-octylnaphthalene The compounds of formula I can be used for the topical and systemic therapy of benign and malignant neoplasms of premalignant lesions and also for the systemic and topical prophylaxis of the said conditions.

Furthermore, they are suitable for the topical and systemic therapy of acne, psoriasis and other dermatoses which are accompanied by an intensified or pathologically altered cornification, as well as of inflammatory and allergic dermatological conditions. Further, the compounds of formula I can also be used for the control of mucous membrane disorders with inflammatory or degenerative or metaplastic changes.

The pharmaceutical preparations can be administered enterally, parenterally or topically. For enteral administration there are suitable e.g. preparations in the form of tablets, capsules, dragees, syrups, suspensions, solutions and suppositories. preparations in the form of infusion or injection solutions are suitable for parenteral administration The dosages in which the preparations are administered can vary according to the mode of use and route of use as well as according to the requirements of the patients. In general, daily doses of about 0.1-50 mg/kg, preferably 1-15 mg/kg, come into consideration for adults.

The preparations can be administered in one dosage or several dosages. Capsules containing about 5-200 mg of active substance are a preferred administration form.

The preparations can contain inert or pharmacodynamically active additives. Tablets or granulates e.g. can contain a series of binding agents, filler materials, carrier substances or diluents. Liquid preparations can be present, for example,. in the form of a sterile solution which is miscible with water. Capsules can contain a filler material or thickening agent in addition to the active substance. Furthermore, flavour-improving additives as well as the substances usually used as preserving, stabilizing, moisture-retaining and emulsifying agents, salts for varying the osmotic pressure, buffers and other additives can also be present.

The previously mentioned carrier substances and diluents can be organic or inorganic substances, e.g. water, gelatine, lactose, starch, magnesium stearate, talc, gum arabic, polyalkylene glycols and the like. It is a prerequisite that all adjuvants used in the manufacture of the preparations are non-toxic.

For topical use the active substances are conveniently used in the form of salves, tinctures creams, solutions lotions, sprays, suspensions and the like. Salves and creams as well as solutions are preferred. These preparations intended for topical use can be manufactured by mixing the compounds of formula I as active ingredients with non-toxic, inert, solid or liquid carriers which are usual in such preparations and which are suitable for topical treatment.

For topical use there are suitable conveniently about 0.1–5%, preferably 0.3–2%, solutions as well as about 0.1–5%, preferably about 0.3–2%, salves or creams.

If desired, the pharmaceutical preparations can contain an antioxidant e.g. tocopherol, N-methyl-γ-tocopheramine, butylated hydroxyanisole or butylated hydroxytoluene.

The following Examples illustrate the invention further. The temperatures are given in degrees Celsius.

EXAMPLE 1

45 g of [1-(5,6,7,8-tetrahydro-5,5,8.8-tetramethyl-2-naphthyl)-ethyl]-triphenylphosphonium bromide are suspended in 200 ml of 1,2-butylene oxide. After the addition of 8 g of 4-fluorobenzaldehyde the mixture is boiled at reflux for 16 hours. After cooling the clear, yellowish solution is poured into 1 l of methanol/water (6:4) and extracted repeatedly with hexane. The organic phase is washed three times with water and, after drying over sodium sulphate evaporated. The crystalline residue can be recrystallized from hexane and gives 11.2 g of (E)-6-(P-fluoro-α-methylstyryl)-1,2,3,4-tetrahydro-1,1,4,4-tetramethylnaphthalene in colourless crystals, melting point 99°–101°.

In an analogous manner there are obtained (E)-6-[p-chloro-α-methylstyryl]-1,2,3,4-tetrahydro-1,1,4,4-tetramethylnaphthalene melting point 125°–126°;

(E)-6-[p-iodo-α-methylstyryl]-1,2.3,4-tetrahydro-1,1,4,4-tetramethylnaphthalene, melting point 124°–126°;

(E)-6-[p-nitro-α-methylstyryl]-1,2,3,4-tetrahydro-1,1,4,4-tetramethylnaphthalene, melting point 164°–165°;

(E)-6-[2-(4-biphenylyl)-1-methylvinyl]-1,2,3,4-tetrahydro-1,1,4,4-tetramethylnaphthalene, melting point 127°–128°;

(E)-6-[m-fluoro-α-methylstyryl]-1,2,3,4-tetrahydro-1,1,4,4-tetramethylnaphthalene, melting point 72°–73°;

(E)-6-[m-bromo-α-methylstyryl]-1,2,3,4-tetrahydro-1,1,4,4-tetramethylnaphthalene melting point 98°–99°;

(E)-6-[o-fluoro-α-methylstyryl]-1,2,3,4-tetrahydro-1,1,4,4-tetramethylnaphthalene, melting point 75°–77°;

(E)-6-[o-bromo-α-methylstyryl]-1,2,3,4-tetrahydro-1,1,4,4-tetramethylnaphthalene, melting point 64°–66°;

1,1,3,3-tetramethyl-5-[(E)-α-methylstyryl]indane, melting point 48°–50°;

1,1,3,3-tetramethyl-5-[(E)-α-methyl-p-nitrostyryl]indane, melting point 149°–150°;

5-(p-fluoro-α-methylstyryl)-1,1,3,3-tetramethylindane, melting point 75°–77°;

5-(p-chloro-α-methylstyryl)-1,1,3,3-tetramethylindane, melting point 96°–98°;

5-(p-iodo-α-methylstyryl)-1,1,3,3-tetramethylindane, melting point 129°–131°;

1,1,3,3-tetramethyl-5-[(E)-p-methoxy-α-methylstyryl]indane, melting point 83°–84°;

1,2,3,4-tetrahydro-1,1-dimethyl-6-(α-methylstyryl)-naphthalene, melting point 46°–48° (from ethanol);

1,2,3,4-tetrahydro-1,1-dimethyl-7-(α-methylstyryl)-naphthalene, melting point 58°–59° (from ethanol);

7-[(E)-p-fluoro-α-methylstyryl]-1,2,3,4-tetrahydro-1,1-dimethylnaphthalene, melting point 64°–65° (from ethanol).

EXAMPLE 2

358 g of [I-(5.6.7.8-tetrahydro-5,5,8 8-tetramethyl-2-naphthyl)-ethyl]-triphenylphosphonium bromide are suspended in 600 ml of tetrahydrofuran and treated at 0° with 400 ml of n-butyllithium (1.6 molar in hexane). After stirring at 0° for 30 minutes a solution of 78.5 g of p-methoxybenzaldehyde in 200 ml of tetrahydrofuran is added dropwise thereto and the mixture is stirred at room temperature for a further 2 hours. The reaction mixture is subsequently poured into 2 l of methanol/water (6:4) and extracted repeatedly with hexane. The organic phase is washed three times with water and, after drying with sodium sulphate, evaporated. The crystalline residue can be recrystallized from hexane and gives 138 g of 1,2,3,4-tetrahydro-6-[(E)-p-methoxy-α-methylstyryl]-1,1,4,4-tetramethylnaphthalene, melting point 108°–110°.

In an analogous manner there are obtained p-[2-(5,6,7,8-Tetrahydro-5,5,8,8-tetramethyl-2-naphthyl)propenyl]phenyl acetate, melting point 114°–116°;

m-[2-(5,6,7,8-tetrahydro-5 5,8,8-tetramethyl-2-naphthyl)propenyl]phenyl acetate, melting point 83°–85°;

o-[2-(5,6,7,8-tetrahydro-5,5,8,8-tetramethyl-2-naphthyl)propenyl]phenyl acetate, melting point 78°–80°;

1,2,3,4-tetrahydro-1,1,4,4-tetramethyl-1-(α,m-dimethylstyryl)naphthalene melting point 106°;

1.2.3 4-tetrahydro-1,1,4,4-tetramethyl-6-(α,o-dimethylstyryl)naphthalene, melting point 61°–62°;

1,2,3,4-tetrahydro-1,1,4,4-tetramethyl-6-(α,3,5-trimethylstyryl)naphthalene, melting point 113°–114°;

1,2,3,4-tetrahydro-1,1,4,4-tetramethyl-6-(α,2,5-trimethylstyryl)naphthalene, melting point 72°;

1,2,3,4-tetrahydro-1,1,4,4-tetramethyl-6-(α,2,6-trimethylstyryl)naphthalene, melting point 78°.

EXAMPLE 3

6 g of 6-[p-nitro-α-methylstyryl)-1,2,3,4-tetrahydro-1,1,4,4-tetramethylnaphthalene are dissolved in 200 ml of acetic acid and, after heating to 90°, treated within 2 minutes with 4.5 g of activated iron powder. Thereafter 60 ml of water are added thereto and, after a further 30 minutes, the mixture is again treated with 60 ml of water. After stirring at 90° for 1 hour the reaction mixture is cooled, diluted with water and extracted with ether. The organic phase is washed with water, dilute soda solution and again with water. After drying with sodium sulphate the organic phase is evaporated and there is obtained a brown oil which is purified by filtration over silica gel (elution agent hexane/acetic acid 4:1). Recrystallization from hexane gives 4.5 g of p-[2-(5.6,7,8-tetrahydro-5,5,8,8-tetramethyl-2-naphthyl)-propenyl]aniline in colourless crystals, melting point 106°–108°.

EXAMPLE 4

320 mg of p-[2-(5.6.7,8-tetrahydro-5,5,8.8-tetramethyl-2-naphthyl)propenyl]aniline are dissolved in 5 ml of acetonitrile and treated at room temperature with 440 mg of acetaldehyde and 190 mg of sodium cyanoborohydride. After 30 minutes the mixture is adjusted to a pH of 6–7 by the addition of acetic acid and 440 mg of acetaldehyde are again added thereto. After stirring at room temperature for 2 hours the reaction mixture is poured into ice-water, made alkaline by the addition of 2N potassium hydroxide solution and extracted with ether. The brownish oil obtained after drying and evaporation of the organic solvent is filtered over silica gel (elution agent hexane/ethyl acetate 9:1) and recrystallized from hexane. There are obtained 280 mg of N,N-diethyl-p-[(E)-2-(5,6,7,8-tetrahydro-5,5,8,8-tetramethyl-2-naphthyl)propenyl]aniline in colourless crystals, melting point 89°–90°.

EXAMPLE 5

6.1 g of (1,2,3,4-tetrahydro-1,1,4,4-tetramethyl-6-naphthyl) ethyl ketone are dissolved in 25 ml of abs. ether and added dropwise at 0° to a benzylmagnesium chloride solution prepared from 0.6 g of magnesium and 4.3 g of benzyl chloride in 30 ml of abs. ether. After stirring at room temperature for 2 hours the reaction mixture is poured into a saturated ammonium chloride solution, extracted with ether, dried over sodium sulphate and evaporated. The thus-obtained oil is dissolved in 100 ml of toluene and, after the addition of 0.5 g of p-tlouenesulphonic acid, boiled at reflux overnight. After cooling the mixture is treated with 10% sodium bicarbonate solution, extracted with ether, dried and evaporated. The residue is purified by filtration over a short column (silica gel, elution agent hexane) and recrystallized from methylene chloride/methanol. There are obtained 3 g of 6-(α-ethylstyryl)-1,2,3,5-tetrahydro-1,1,4,4-tetramethylnaphthalene in colourless crystals, melting point 65°.

EXAMPLE 6

1.1 g of sodium hydride (50% in mineral oil) are washed with abs. pentane, dried and suspended in 20 ml of dimethylformamide. While cooling with ice there is added dropwise thereto a solution of 5.3 g of diethyl benzylphosphonate in 50 ml of dimethylformamide. After 1 hour a solution of 5 g of 1,2,3,4-tetrahydro-1,1,4,4-tetramethyl -6-naphthyl aldehyde in 40 ml of dimethylformamide is allowed to drop in and the mixture is stirred at 40° overnight. The reaction mixture is poured on to ice, extracted repeatedly with ether, dried and evaporated. In order to separate the Z-isomer, the thus-obtained oil is chromatographed (silica gel elution agent hexane) and recrystallized from hexane. There are obtained 4.1 g of (E) -1,2,3,4-tetrahydro-1,1,4,4-tetramethyl-6-styrylnaphthalene in colourless crystals, melting point 57°–58°.

EXAMPLE 7

In analogy to Example 6. by the Wittig-Horner reaction of 6.8 g 8-tetrahydro-5,5,8,8-tetramethyl-2-naphthyl)methanephosphonate with 2.4 g of acetophenone there are obtained, after recrystallization from methanol, 1.5 g of (E)-1,2,3,4-tetrahydro-1,1,4,4-tetramethyl-6-(β-methylstyryl)naphthalene in colourless crystals, melting point 72°–73°.

The phosphonate used in this Example can be prepared in a simple manner starting from 1.2,3,4-tetrahydro-1,1,4,4-tetramethyl-6-naphthyl aldehyde by reduction with sodium borohydride in ethanol to the corresponding hydroxymethyl compound (melting point 78° from pentane), conversion into the bromomethyl compound (boiling point 125° /0.01 mm) by reaction with phosphorus tribromide and reaction with triethyl phosphite (16 hours, 150°, melting point 55° from hexane).

EXAMPLE 8

In analogy to Example 1 from 20 g of [1-(5,6,7,8-tetrahydro-2-naphthyl)ethyl]triphenylphosphonium bromide and 4 g of benzaldehyde there are obtained, after chromatography (silica gel, elution agent hexane), 4.6 g of 1,2,3,4-tetrahydro-6-(α-methylstyryl)naphthalene as a colourless oil, boiling point about 170°/0.01 mm.

EXAMPLES 9

A solution of diethyl benzylphosphonate in 30 ml of dimethylformamide is added at room temperature to a suspension of 3.7 g of NaH (50% in mineral oil) in 50 ml of dimethylformamide. After stirring at room temperature for 15 minutes a solution of 12.6 g of 7-acetyl-1,1,4,4,6-pentamethyltetralin in 60 ml of dimethylformamide is added dropwise thereto in the course of 2 hours. The reaction mixture is stirred at room temperature overnight and subsequently heated to 60° for a further 1 hour. After cooling the mixture is poured on to ice, extracted with ether, dried and evaporated. After chromatography of the crude product (silica gel, elution agent hexane) and crystallization from hexane there are obtained 3.9 g of 1,2,3,4-tetrahydro-1,1,4,4,7-pentamethyl-6-[(E)-α-methylstyryl]naphthalene in colourless crystals, melting point 75°–77°.

EXAMPLE 10

In analogy to Example 9, from diethyl benzylphosphonate and 5,6,7,8-tetrahydro-5,5,8,8-tetramethyl-3-octyl-2-acetonaphthone there is manufactured 1,2,3,4-tetrahydro-1,1,4,4-tetramethyl-6-(α-methylstyryl)-7-octylnaphthalene, melting point 47°–48° (from hexane).

EXAMPLE 11

In analogy to Example 1, from 7.1 g of [1-(1,1,3,3-tetramethyl-indan-2-on-5-yl)ethyl]triphenylphosphonium bromide and 1.4 g of benzaldehyde there are obtained, after chromatography (silica gel, elution agent hexane/ether=9:1) and recrystallization from hexane, 800 mg of 1,1,3,3-tetramethyl-5-[(E)-α-methylstyryl]-2-indanone, melting point 83°–85°.

The phosphonium bromide used as the starting material can be prepared in a simple manner by the Friedel-Crafts acetylation of 1,1,3,3-tetramethylindanone, reduction of the acetyl group with sodium borohydride and reaction with triphenylphosphonium bromide.

EXAMPLE 12

1.4 g of 1,1,3,3-tetramethyl-5-[(E)-α-methylstyryl]-2-indanone are dissolved in 100 ml of ethanol and treated at room temperature with 6 g of sodium borohydride. After stirring at room temperature for 16 hours the reaction mixture is poured on to ice and extracted repeatedly with ether. The organic phase is washed with saturated sodium chloride solution dried and evaporated. The residue can be recrystallized from hexane and gives 1.1 g of 1,1,3,3-tetramethyl-5-[(E)-α-methylstyryl]-2-indanol in colourless crystals, melting point 63°–67°.

EXAMPLE 13

2.80 g of 6'-(tert-butyldimethylsiloxy)-5',6',7',8'-tetrahydro -5',5',8',8'-tetramethyl-2-acetonaphthone in 10 ml of abs. THF are added dropwise at 0° to a Grignard solution prepared from 1.90 g of benzyl chloride and 437 mg of Mg shavings in 30 ml of abs. THF. After 15 minutes the mixture is hydrolyzed with H$_2$O, extracted with ether and the organic phases are washed thoroughly with H$_2$O. After drying and removing the solvent the residue, a viscous oil, is taken up in 20 ml of CH$_2$Cl$_2$ and treated with 150 mg of p-toluenesulphonic acid. After 6 hours the mixture is filtered over silica gel and the crude product is treated at 40° for about 14 hours with 6.3 g of nBu$_4$NF.3H$_2$O in 20 ml of THF. The reaction product is partitioned between water and ether, and the organic phase is washed with water, dried and evaporated. Filtration over silica gel yields 2.27 g of an oil which contains all three possible double bond isomers. In order to equilibrate this, the oil is treated with 200 mg of p-toluenesulphonic acid in 20 ml of CHCl$_3$ at 45°–50°. After 24 hours it is chromatographed over a short silica gel column (petroleum ether: AcOEt=7:3) and recrystallized from hexane. A single repetition of the isomerization with the mother liquor yields a total of 1.32 g of 1,2,3,4-tetrahydro-1,1,4,4-tetramethyl-6[(E)-α-methylstyryl]-2-naphthalenol, m.p. 102°–103°.

The starting material can be obtained as follows:

p-Bromophenylacetic acid is converted by double alkylation conversion into the acid chloride and tandem Friedel-Crafts reaction of the acid chloride with isobutylene under SnCl$_4$ or AlCl$_3$ catalysis into 6-bromo3,4-dihydro-1,1,4,4-tetramethyl-2(1H)-naphthalenone, from which by NaBH$_4$ reduction and silylation with TBDMS Cl/imidazole there is obtained [(6-bromo-1,2,3,4-tetrahydro-1,1,4,4-tetramethyl-2-naphthyl)oxy]tert.-butyldimethylsilane. Grignard reaction with acetaldehyde and MnO$_2$ oxidation yields 6'-(tert-butyldimethylsiloxy)5',6',7',8'-tetrahydro -5',5',8',8'-tetramethyl-2-acetonaphthone.

EXAMPLE 14

In analogy to Example 13, from benzylmagnesium chloride and 7'-(tert-butyldimethylsiloxy)-5',6',7',8'-tetrahydro -5',5',8',8'-tetramethyl-2-acetonaphthone there is obtained 1,2,3,4-tetrahydro-1,1,4,4-tetramethyl7-[(E)-α-methylstyryl]-2-naphthalenol, m.p. 89°–91°.

The starting material can be obtained as follows:

m-Bromobenzyl cyanide is converted by double alkylation and basic hydrolysis into 2-(m-bromophenyl)-2-methylpropionic acid which is further converted in analogy to the process steps described in Example 13 via 7-bromo-3,4-dihydro-1,1,4,4-tetramethyl-2(1H)-naphthalenone.

EXAMPLE 15

144 mg of a 50% sodium hydride dispersion are suspended in 3 ml of dimethylformamide and treated with 740 mg of diethyl fluorophenylmethanesulphonate (prepared from benzyl fluoride by radical bromination with N-bromosuccinimide and reaction with triethyl phosphite). After stirring at room temperature for 2 hours 1.15 g of 5,6,7,8-tetrahydro-5,5,8,8-tetramethyl-2-acetonaphthone are added dropwise thereto and the mixture is heated at 55° overnight. After cooling the mixture is poured into ice-water and extracted with ether. After drying and evaporating the organic phase there are obtained 1.3 g of crude product which is purified by chromatography on silica gel (elution agent hexane/ethyl acetate =99:1) and, after recrystallization from hexane, there are obtained 77 mg of 6-[(Z)-α-fluoro-α-methylstyryl]-1,2,3,4-tetrahydro-1,1,4,4-tetramethylnaphthalene m.p. 100°.

Example 16

In analogy to Example 1, from 19.4 g of [1-(1,1,3,3-tetramethyl-5-indanyl)ethyl]triphenylphosphonium bromide, 6.9 g of ethyl P-formylphenylcarbonate and 200 ml of butylene oxide there are obtained, after filtration of the crude product over silica gel (elution agent hexane/ethyl acetate =19:1), 5 g of ethyl p-[2-(1,1,3,3-tetramethyl-5-indanyl)propenyl]phenylcarbonate as a yellowish oil which solidifies in the cold and which can be recrystallized from hexane. 5 g of the thus-obtained product are dissolved in 50 mg of ethanol and treated with a solution of 7.4 g of potassium hydroxide in 25 ml of water. After stirring at room temperature for 3 hours the mixture is poured into ice-water, acidified with 3N hydrochloric acid, extracted with ethyl acetate and evaporated. After recrystallization of the crude product from hexane there are obtained 2.6 g of p-[2-(1,1,3,3-tetramethyl-5-indanyl)propenyl]phenol in colourless crystals, m.p. 137°.

The ethyl p-formylphenylcarbonate used as the starting material can be prepared in a simple manner by reacting p-hydroxybenzaldehyde with ethyl chloroformate with the addition of triethylamine. Distillation of the crude product gives ethyl p-formylphenylcarbonate as a colourless liquid, b.p. 111–113° /2.5 mm.

EXAMPLE 17

In analogy to Example 1, from 21.9 g of [1-(1,1,3,3-tetramethyl-indan-2-on-5-yl)ethyl]triphenylphosphonium bromide, 7.6 g of ethyl p-formylphenylcarbonate and 400 ml of butylene oxide there are obtained, after filtration of the crude product over silica gel (elution agent hexane/ethyl acetate =4:1) and recrystallization from hexane/ethyl acetate, 3.4 g of ethyl p-[2-(1,1,3,3-tetramethyl-2-oxo-5-indanyl)propenyl]phenylcarbonate, m.p, 130°–131°.

Hydrolysis of this product with an excess of potassium hydroxide in ethanol/water gives, after recrystallization from ethyl acetate/hexane, 1.7 g of 5-(p-hydroxy-α-methylstyryl)-1,1,3,3-tetramethyl-2-indanone in colourless crystals, m.p. 172–173°.

EXAMPLE 18

A solution of 1 g of 5-(p-hydroxy-α-methylstyryl)-1,1,3,3-retramethyl-2-indanone in 10 ml of tetrahydrofuran is added dropwise while cooling with ice to a suspension of 100 mg of lithium aluminium hydride in 5 ml of tetrahydrofuran and the mixture is subsequently left to stir at room temperature for 2 hours. After the dropwise addition of 50 ml of 2N hydrochloric acid at 0° the mixture is extracted with ethyl acetate and the organic phase is washed with water, dried and evaporated. After filtration of the crude product over silica gel (elution agent hexane/ethyl acetate 1:1) it is recrystallized from ethyl acetate/hexane and there are obtained 500 mg of 5-(p-hydroxy-α-methylstyryl)-1,1,3,3-tetramethyl-2-indanol in colourless crystals, m.p. 148°–149°.

EXAMPLE 19

In analogy to Example 2, from [1-(5,6,7,8-tetrahydro-3-methoxy-5,5,8,8-tetramethyl-2-naphthyl)ethyl]-triphenylphosphonium bromide and ethyl p-formylphenylcarbonate there is obtained ethyl [p-[(E)-2-(5,6,7,8-tetrahydro-3-methoxy-5,5,8,8-tetramethyl-2-naphthyl)-propenyl]phenyl]-carbonate m.p. 122°–123°.

Hydrolysis of this product with an excess of potassium hydroxide in ethanol/water gives, after recrystallization from methanol P-[(E)-2-(5,6,7,8-tetrahydro-3-methoxy-5,5,8,8-tetramethyl-2-naphthyl)propenyl]-phenol, m.p. 181°.

EXAMPLE 20

In analogy to Example 5,
from 7-acetyl-6-chloro-1,2,3,4-tetrahydro-1,1,4,4-tetramethylnaphthalene and benzylmagnesium chloride there is obtained (E)-6-chloro-1 2,3,4-tetrahydro-1,1,4,4-tetramethyl-7-(α-methylstyryl)naphthalene m.p. 114°, from 7-acetyl-1,2,3,4-tetrahydro-6-methoxy-1,1,4 4-tetramethylnaphthalene and benzylmagnesium chloride there is obtained (E)-1,2,3,4-tetrahydro-7-methoxy-6-(α-methylstyryl)-1,1,4,4-tetramethylnaphthalene. m.p. 88°–89°, and from 7-acetyl-1,2,3,4-tetrahydro-5,8-dimethoxy-1,1,4,4- tetramethylnaphthalene and benzylmagnesium chloride there is obtained (E)-1,2,3,4-tetrahydro-5,8-dimethoxy-6-(α- methylstyryl)naphthalene. m.p. 110°.

The manufacture of dosage forms of the compounds of formula I can be effected in the usual manner, e.g. on the basis of the following Examples.

EXAMPLE A

Hard gelatine capsules can be manufactured as follows:

| Ingredients | mg/capsule |
| --- | --- |
| 1. Spray-dried powder containing 75% of compound I | 200 |
| 2. Sodium dioctl sulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 300 |

The spray-dried powder, which is based on the active substance, gelatine and microcrystalline cellulose and which has an average particle size of the active substance of $<1\mu$ (measured by means of autocorrelation spectroscopy), is moistened with an aqueous solution of sodium carboxymethylcellulose and sodium dioctyl sulphosuccinate and kneaded. The resulting mass is granulated, dried and sieved, and the granulate obtained is mixed with microcrystalline cellulose, talc and magnesium stearate. The powder is filled into size O capsules.

EXAMPLE B

Tablets can be manufactured as follows:

| Ingredients: | mg/tablet |
| --- | --- |
| 1. Compound I as a finely milled powder | 500 |
| 2. Lactose powd. | 100 |
| 3. Maize starch white | 60 |
| 4. Povidone K30 | 8 |

-continued

| Ingredients: | mg/tablet |
| --- | --- |
| 5. Maize starch white | 112 |
| 6. Talc | 16 |
| 7. Magnesium stearate | 4 |
| Total | 800 |

The finely milled substance is mixed with lactose and a portion of the maize starch. The mixture is moistened with an aqueous solution of Povidone K30 and kneaded, and the resulting mass is granulated, dried and sieved. The granulate is mixed with the remaining maize starch, talc and magnesium stearate and pressed to tables of suitable size.

EXAMPLE C

Soft gelatine capsules can be manufactured as follows:

| Ingredients | mg/capsule |
| --- | --- |
| 1. Compound I | 50 |
| 2. Triglyceride | 450 |
| Total | 500 |

10 g of compound I are dissolved in 90 g of medium-chain triglyceride with stirring, inert gasification and protection from light. This solution is processed as the capsule fill mass to soft gelatine capsules containing 50 mg of active substance.

EXAMPLE D

A lotion can be manufactured as follows:

| Ingredients | |
| --- | --- |
| 1. Compound I, finely milled | 3.0 g |
| 2. Carbopol 934 | 0.6 g |
| 3. Sodium hydroxide | q.s. ad pH 6 |
| 4. Ethanol, 94% | 50.0 g |
| 5. Demineralized water | ad 100.0 g |

The active substance is incorporated into the ethanol, 94%/water mixture under protection from light. Carbopol 934 is stirred in until gelling is complete and the pH value is adjusted with sodium hydroxide.

We claim:

1. A compound of the formula:

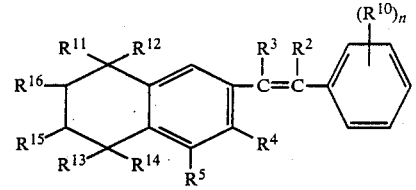

wherein n is $R^2$ and $R^3$ are hydrogen, lower alkyl, trifluoromethyl or halogen; with one of $R^2$ and $R^3$ being hydrogen, lower alkyl or trifluromethyl; $R^4$ and $R^5$ are hydrogen, alkyl, alkoxy or halogen; $R^{11}$, $R^{12}$, $R^{13}$ and $R^{14}$ are hydrogen or methyl; $R^{10}$ is p-fluoro; and $R^{15}$ and $R^{16}$ are hydrogen, oxo, lower alkyl, acyloxy, hydroxy or lower alkoxy; with the proviso that both $R^{15}$ and $R^{16}$ are not oxo.

2. The compound of claim 1 wherein said olefinic double bond has the trans configuration.

3. The compound of claim 2 wherein said compound is (E)-6-(p-fluoro-α-methylstyryl)-1,1,3,4-tetrahydro-1,1,4,4-tetramethylnaphthalene.

4. The compound of claim 2 wherein said compound is 6-1,2,3,4-tetrahydro-1,1, 4,4-tetramethylnaphthalene.

* * * * *

UNITED STATES PATENT AND TRADEMARK OFFICE
CERTIFICATE OF CORRECTION

PATENT NO. : 4,935,560

DATED : June 19, 1990

INVENTOR(S) : Klaus et al.

It is certified that error appears in the above-identified patent and that said Letters Patent is hereby corrected as shown below:

Column 16 line 54 "wherein n is $R^2$ and $R^3$ are hydrogen, lower alkyl, triflu-" should be wherein n is an integer from 1 $R^2$ and $R^3$ are hydrogen, lower alkyl, triflu- Column 16 line 67 " is 6-1,2,3,4-tetrahydro-1,1,4,4-tetramethylnaphthalene." should be 6-[(Z)-p-Fluoro-a-methylstyryl]-1,2,3,4-tetrahydro-1,1,4,4-tetramethylnaphthalene.

Signed and Sealed this

Tenth Day of September, 1991

Attest:

HARRY F. MANBECK, JR.

Attesting Officer

Commissioner of Patents and Trademarks